US011475995B2

(12) United States Patent  
Madhavan et al.

(10) Patent No.: US 11,475,995 B2  
(45) Date of Patent: Oct. 18, 2022

(54) INTEGRATION OF MULTI-OMIC DATA INTO A SINGLE SCORING MODEL FOR INPUT INTO A TREATMENT RECOMMENDATION RANKING

(71) Applicant: PERTHERA, INC., McLean, VA (US)

(72) Inventors: Subha Madhavan, Potomac, MD (US); Robert Joseph Bender, Rockville, MD (US); Emanuel Frank Petricoin, III, Gainesville, VA (US)

(73) Assignee: PERTHERA, INC., McLean, VA (US)

( * ) Notice: Subject to any disclaimer, the term of this patent is extended or adjusted under 35 U.S.C. 154(b) by 63 days.

(21) Appl. No.: 16/405,640

(22) Filed: May 7, 2019

(65) Prior Publication Data  
US 2019/0385740 A1    Dec. 19, 2019

Related U.S. Application Data

(60) Provisional application No. 62/667,927, filed on May 7, 2018.

(51) Int. Cl.  
*G16H 50/50* (2018.01)  
*G16H 20/10* (2018.01)  
(Continued)

(52) U.S. Cl.  
CPC .............. *G16H 50/20* (2018.01); *G16B 5/20* (2019.02); *G16H 20/10* (2018.01); *G16H 50/50* (2018.01)

(58) Field of Classification Search  
CPC ........ G16H 50/30; G16H 50/70; G16H 10/60; G16H 20/10; G16H 20/00; G06N 20/00; G06N 3/0454; G06N 3/123  
See application file for complete search history.

(56) References Cited

U.S. PATENT DOCUMENTS

2008/0261820 A1 * 10/2008 Iyengar ................. G16B 40/00  
506/8  
2015/0019239 A1 * 1/2015 Ebadollahi ............. G16H 50/50  
705/2

(Continued)

FOREIGN PATENT DOCUMENTS

WO    WO-2013011479 A2 *  1/2013  .............. C12Q 1/68

OTHER PUBLICATIONS

Coker, Elizabeth A., et al. "SiGNet: A signaling network data simulator to enable signaling network inference." Plos one 12.5 (2017): e0177701. (Year: 2017).*

*Primary Examiner* — Linh Giang Le  
*Assistant Examiner* — Constantine Siozopoulos  
(74) *Attorney, Agent, or Firm* — Troutman Pepper Hamilton Sanders LLP

(57) ABSTRACT

A method and system for determining a recommendation for drug treatment are described herein. For example, the method includes determining drug scores based upon network-based distances for one or more target drug nodes, modeling one or more outputs based upon input data, wherein the input data comprises at least a portion of the drug scores, selecting an algorithmic output from the one or more modeling outputs based upon at least one performance criteria, determining if the selected algorithmic output of the modeling satisfies a threshold, and if the selected algorithmic output satisfies the threshold, generating the recommendation for drug treatment. The system includes a processing device and computer readable medium including programming instructions that, when executed, cause the processing device to perform the method as described herein.

46 Claims, 9 Drawing Sheets

(51) Int. Cl.
*G16B 5/20* (2019.01)
*G16H 50/20* (2018.01)

(56) References Cited

U.S. PATENT DOCUMENTS

| | | |
|---|---|---|
| 2015/0363559 A1 | 12/2015 | Jackson et al. |
| 2016/0224760 A1 | 8/2016 | Petak et al. |
| 2016/0232309 A1* | 8/2016 | Yoon ........................ G16H 50/20 |
| 2018/0039731 A1* | 2/2018 | Szeto ...................... G16B 40/20 |
| 2018/0357372 A1 | 12/2018 | Bagaev et al. |
| 2019/0057182 A1 | 2/2019 | Klement et al. |
| 2019/0341153 A1 | 11/2019 | Ng et al. |
| 2020/0185063 A1 | 6/2020 | Narain et al. |
| 2020/0411199 A1 | 12/2020 | Shrager et al. |

* cited by examiner

INTEGRATION OF MULTI-OMIC DATA INTO A SINGLE SCORING MODEL FOR INPUT INTO A TREATMENT RECOMMENDATION RANKING

CROSS-REFERENCE TO RELATED APPLICATION

This application claims priority to and the full benefit of U.S. Provisional Patent Application No. 62/667,927, filed May 7, 2018 and entitled INTEGRATION OF MULTI-OMIC DATA INTO A SINGLE SCORING MODEL FOR INPUT INTO A TREATMENT RECOMMENDATION RANKING. The entirety of U.S. Provisional Patent Application No. 62/667,927 is incorporated by reference herein.

TECHNICAL FIELD

The present disclosure relates to processes and techniques for recommending treatment for a patient using a variable weighting-based scoring algorithm. More specifically, the present disclosure uses a scoring algorithm where certain molecular data is more highly weighted than other molecular data.

BACKGROUND

Genetic information from patients allows the possibility of precision oncology and treatments for patients that are individualized. However, genetic information alone may not be sufficient. For example, a genomic profiling study reveals actionable mutations affecting signaling pathways, but in spite of these mutations, targeted inhibitors of these pathways may have low success rates. A possible reason for these failures is that single-gene biomarkers may fail to account for crosstalk within and between dysregulated pathways. Multi-omic profiling based on multiple biomarkers, genetic and molecular information, and patient history can help make better molecular recommendations for treatment.

There has been an explosion in the number of drugs being developed specifically for cancer—nearly 1,000 of them are now at various stages of being tested for safety and efficacy. This growth in new drugs is associated with an evolution of precision medicine. However, it is unlikely that an oncologist or an entire oncology team treating a particular patient can keep up with all the science and progress being established by these clinical trials or keep up with all of the published literature on disease treatments. Additionally, recommending treatment based upon previous treatment history, disease relevance, and molecular data does not take into consideration variable weighting of different molecular data that should be considered based upon, for example, relative importance and proximity of the data/biomarker(s) to the mechanism of action for a given therapeutic.

Accordingly, there remains a need for a system and process of treatment recommendation that weights specific molecular data (e.g., phosphoprotein data) higher than other molecular data when generating a single molecular score to be used to recommend or rank treatment options.

SUMMARY

A method for determining a recommendation for drug treatment is described herein. In certain implementations, the method includes determining drug scores based upon network-based distances for one or more target drug nodes, modeling one or more outputs based upon input data, wherein the input data comprises at least a portion of the drug scores, selecting an algorithmic output from the one or more modeling outputs based upon at least one performance criteria, determining if the selected algorithmic output of the modeling satisfies a threshold, and if the selected algorithmic output satisfies the threshold, generating the recommendation for drug treatment.

A system for determining a recommendation for drug treatment is also described herein. In certain implementations, the system includes a processing device and a computer readable medium operably connected to the processing device. The computer readable medium can include programming instructions that, when executed, cause the processing device to determine drug scores based upon network-based distances for one or more target drug nodes, model one or more outputs based upon input data, wherein the input data comprises at least a portion of the drug scores, select an algorithmic output from the one or more modeling outputs based upon at least one performance criteria, determine if the selected algorithmic output of the modeling satisfies a threshold, and if the selected algorithmic output satisfies the threshold, generate the recommendation for drug treatment.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings.

DETAILED DESCRIPTION

Figure 1A:
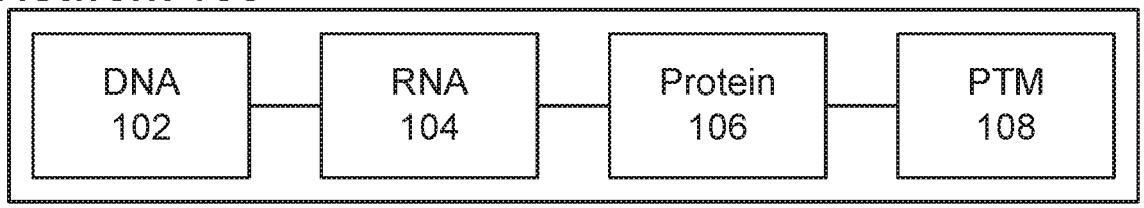
FIG. 1A depicts a network 100 for recommending disease treatment for patients and doctors, in accordance with an example of the present disclosure.

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

The embodiments of the present teachings described below are not intended to be exhaustive or to limit the teachings to the precise forms disclosed in the following detailed description. Rather, the embodiments are chosen and described so that others skilled in the art may appreciate and understand the principles and practices of the present teachings.

The present disclosure is directed to a process for weighting therapeutic significance of alterations in a patient's molecular profile using a network-based distance metric. The key rationale underpinning this invention is that molecular alterations in closer proximity to drug targets have a higher likelihood of signifying drug response than alterations located further away in the network. In certain implementations, two basic types of input data can be used: (1) molecular data generated from a patient tumor specimen; and (2) a biomolecular interaction network. For example, the molecular data can be any combination of multi-omic data. Frequent data types can include genomic, transcriptomic, proteomic, and phosphoproteomic, but the processes and techniques as described herein are flexible and can accept other data types such as epigenetic and other post-translational modifications as well. Typical applications of the invention will utilize data from commercial laboratories, but research/investigational use only data can also be used as input.

The techniques and processes as described herein can also make use of a biomolecular interaction network containing representations of various types of reactions that occur in within signaling pathways of biological systems. In certain implementations, publicly available network databases, such as Reactome and the National Cancer Institute Pathway Interaction Database, can form the basis of this network. The basic network can be expanded so that each distinct protein includes nodes for DNA, RNA, protein, and all activity states of the protein (if applicable). For example, the public network databases generally include the HER2/ERBB2 protein and its active phosphorylated form. The network used in the present disclosure could be expanded to include the DNA and mRNA encoding HER2 as well. In certain implementations as described herein, the expanded network used in the weighting algorithm can be a structured as a graph with directed edges.

A sample process for determining a drug-specific score as taught herein can include various steps. For example, a sample process can include overlaying patient molecular data onto a network graph representation of cellular signaling pathways, computing network proximity-based distance, and extracting a score for nodes corresponding to drug targets.

For example, regarding overlaying the patient molecular data, a corresponding node in the graph will be determined for each molecular result in the patient profile. Gene copy number changes can be mapped to DNA nodes, transcript over-/under-expression can be mapped to mRNA nodes, protein expression changes can be mapped to protein nodes, and phosphoprotein expression changes can be mapped to the active protein nodes. Mutations may typically be mapped to active protein nodes since pathogenic mutations generally affect the structure and function of a protein.

To continue the above example, for computing distances, the locations of the mapped nodes within the network can be compared to the location of known drug targets. The shortest path between each mapped node and drug target node can be computed through, for example, standard graph theory methodologies, such as Dijkstra's algorithm. Alternatively, in certain implementations, the proximity of the entire patient molecular profile to a drug target node can be evaluated by jointly assessing the mapped nodes using a graph diffusion algorithm.

For extracting a score, the minimum network-based distance for each drug target node can be extracted and converted to a drug-specific score. The score can be inversely proportional to the shortest mapped node distance, i.e., if a mapped node corresponding to a molecular alteration is only one node away from the drug target node, the drug-specific score will likely be very high.

Determining the score for a specific drug represents a first key concept of the present disclosure. A second key concept can include refining derived weights for the drug(s) using outcome data and, for example, a closed loop algorithm to perform statistical and machine learning modeling. In certain implementations, the outcomes data can include overall survival information, progression-free survival data for a specific drug, response rate to a specific drug, and other similar outcome data.

For example, a procedure for refining weights can involve testing a variety of statistical and machine learning modeling techniques and selecting the one that performs best. For a given set of biomarker-drug weights, multiple models can be trained to predict the outcomes variable of interest. The best model can be selected, or a combination or averaging of the best models can be generated, and if the best model accuracy is above a pre-specified threshold, then the model and weights will be accepted. If the accuracy is not high enough, the biomarker-drug weights will be adjusted. In certain implementations, rules can be in place to determine what alterations are made to the weights. The entire testing procedure can then be repeated until either the accuracy threshold has been reached, or until all permissible weights have been exhausted. In certain implementations, the modeling techniques can include penalized regression/classification, Bayesian belief networks, collaborative filters, and other similar modeling techniques. More specifically, using penalized regression/classification, overall or progression-free survival can be modeled using regression methods, while response rates can be modeled using classification methods. Penalizing the coefficients of the model can allow for irrelevant or highly correlated features to be downweighted. Coefficient penalties can take the form of ridge (L2 norm), lasso (L1 norm), or a mix of both. Using Bayesian belief networks, joint probability distribution of data can be modeled along with the outcomes variable of interest. The structure of the network can be learned from correlations or mutual information between variables. Using collaborative filters, graph-regularized non-negative matrix factorization (NMF) can be used to model an incomplete matrix of treatment responses. "Missing" responses (i.e. treatments that patients have not received) can be filled in based on the response that other patients have had. Molecular similarity, in the form of the graph defined above for determining unweighted molecular proximity, feeds directly into this algorithm as graph regularization.

Both concepts of determining the drug-specific distance and weighting information as well as modeling the outcome data to refine the drug weighting information are described below in greater detail with regard to the specific figures.

FIG. 1A depicts a network 100 according to an embodiment for recommending disease treatment for patients or doctors. Referring to FIG. 1A, according to some embodiments of the invention, network 100 may include at least one node. In a further embodiment, network 100 may include a deoxyribonucleic acid (DNA) node 102, a ribonucleic acid (RNA) node 104, a protein node 106, or a post-translational modification (PTM) node 108.

In some embodiments the DNA node 102 may comprise one database or multiple databases that may be centralized or distributed. The DNA node 102 may comprise one database or multiple databases that may be publically available. Non-limiting examples of publically available databases include Gene Expression Omnibus, ArrayExpress, Expression Atlas, Genevestigator, RefEx, or NONCODE. There may also be one schema or multiple schemas for accessing the databases. In some embodiments, the DNA node 102 comprising multiple databases may be combined in one or multiple databases. In further embodiments, the DNA node 102 may comprise one database or multiple databases acquired through DNA sequencing as will be apparent to one skill in the art. DNA sequencing may include Maxam-Gilbert sequencing, chemical sequencing, Sanger sequencing, chain-termination sequencing, next generation sequencing, real-time sequencing, Ion Torrent sequencing, pyrosequencing, Illumina sequencing, SOLiD sequencing, nanopore sequencing, massively parallel signature sequencing, polony sequencing, 454 pyrosequencing, DNA nanoball sequencing, Heliscope single molecule sequencing, single molecule real time sequencing, tunneling current sequencing, sequencing by hybridization, sequencing with mass spectrometry, microfluidic Sanger sequencing, transmission electron microscopy sequencing, RNA polymerase sequencing, DNA sequencing, DNA microarray, RNA sequencing, RNA microarray, DNA modification sequencing, RNA modification sequencing, epigenetic sequencing, bisulfite sequencing, serial analysis of gene expression, cap analysis of gene expression, or a combination thereof.

In some embodiments the RNA node 104 may comprise one database or multiple databases that may be centralized or distributed. The RNA node 104 may comprise one database or multiple databases that may be publically available. Non-limiting examples of publically available databases include Gene Expression Omnibus, ArrayExpress, Expression Atlas, Genevestigator, RefEx, or NONCODE. There may also be one schema or multiple schemas for accessing the databases. In some embodiments, the RNA node 104 comprising multiple databases may be combined in one or multiple databases. In further embodiments, the RNA node 104 may comprise one database or multiple databases acquired through RNA sequencing as will be apparent to one skill in the art. In additional embodiments, the RNA node 104 may comprise one database or multiple databases acquired through RNA sequencing. RNA sequencing may comprise sequencing species of RNA. Non-limiting examples of species of RNA include mRNA, tRNA, rRNA, 5S rRNA, small nuclear RNA, small nucleolar RNA, small subunit rRNA, large subunit rRNA, NoRC RNA, promoter RNA, SmY RNA, small cajal body-specific RNA, guide RNA, ribonuclease P, ribonuclease MRP, Y RNA, telomerase RNA component, spliced leader RNA, antisense RNA, cis-natural antisense transcript, antisense micro RNA, double stranded RNA, CRISPR RNA, non-coding RNA, long non-coding RNA, long intergenic non-coding RNA, non-messenger RNA, small RNA, small non-messenger RNA, soluble RNA, protein coding RNA, micro RNA, piwi-interacting RNA, small interfering RNA, short hairpin RNA, trans-acting siRNA, repeat associated siRNA, 7SK RNA, or enhancer RNA.

In some embodiments, RNA sequencing may include Maxam-Gilbert sequencing, chemical sequencing, Sanger sequencing, chain-termination sequencing, next generation sequencing, real-time sequencing, Ion Torrent sequencing, pyrosequencing, Illumina sequencing, SOLiD sequencing, nanopore sequencing, massively parallel signature sequencing, polony sequencing, 454 pyrosequencing, DNA nanoball sequencing, Heliscope single molecule sequencing, single molecule real time sequencing, tunneling current sequencing, sequencing by hybridization, sequencing with mass spectrometry, microfluidic Sanger sequencing, transmission electron microscopy sequencing, RNA polymerase sequencing, DNA sequencing, DNA microarray, RNA sequencing RNA microarray, DNA modification sequencing, RNA modification sequencing, epigenetic sequencing, bisulfite sequencing, serial analysis of gene expression, cap analysis of gene expression, or a combination thereof.

In some embodiments the protein node 106 may comprise one database or multiple databases that may be centralized or distributed. The protein node 106 may comprise one database or multiple databases that may be publically available. A non-limiting example of a publically available database includes the proteomics identifications (PRIDE) database. There may also be one schema or multiple schemas for accessing the databases. In some embodiments, the protein node 106 comprising multiple databases may be combined in one or multiple databases. In further embodiments, the protein node 106 may comprise one database or multiple databases acquired through proteomics as will be apparent to one skill in the art. Proteomics may include western blot analysis, enzyme-linked assays, suspension bead assays, immunohistochemical staining, immunofluorescence staining, enzyme linked immunosorbent assay, mass spectrometry, matrix-assisted laser desorption/ionization (MALDI) spectrometry, time of flight (TOF) spectrometry, MALDI-TOF spectrometry, electrospray ionization (ESI) spectrometry, protein chips, reverse-phased protein microarrays, ion mobility spectrometry or any other method of measuring protein amount as apparent to one skilled in the art.

In further embodiments, the protein node 106 may comprise one database or multiple databases acquired through metabolomics as will be apparent to one skill in the art. Metabolomics may comprise one database or multiple databases that may be publically available. A non-limiting example of a publically available database includes the Human Metabolome database. Metabolomics may include mass spectrometry, gas chromatography, high performance liquid chromatography, liquid chromatography, capillary electrophoresis, nuclear magnetic resonance (NMR) spectroscopy, atmospheric pressure chemical ionization, secondary ion mass spectrometry, desorption electrospray ionization, ion mobility spectrometry, or any other method of measuring metabolites as apparent to one skilled in the art.

In some embodiments the PTM-node 108 may comprise one database or multiple databases that may be centralized or distributed. The PTM node 108 may comprise one database or multiple databases that may be publically available. Non-limiting examples of publically available databases include the dbPTM, ProteomeScout, and Phospho- SitePlus database. There may also be one schema or multiple schemas for accessing the databases. In some embodiments, the PTM node 108 comprising multiple databases may be combined in one or multiple databases. As understood by one skilled in the art, non-limiting examples of post-translational modifications which comprise the PTM-node 108 may include myristoylation, palmitoylation, isoprenylation, prenylation, farnesylation, geranylgeranylation, glypiation, glycosylphosphatidylinositol (GPI) anchor, lipoylation, Flavin moiety, heme C attachment, phosphopantetheinylation, acylation, acetylation, formylation, alkylation, methylation, arginylation, polyglutamylation, polyglycylation, butyrylation, gamma-carboxylation, glycosylation, polysialylation, malonylation, hydroxylation, iodination, ribosylation, ADP-ribosylation, phosphorylation, adenylylation, propionylation, pyroglutamate, glutathionylation, S-glutathionylation, nitrosylation, S-nitrosylation, sulfenylation, sulfinylation, sulfonylation, succinylation, sulfation, glycation, carbamylation, carbonylation, biotinylation, carbamylation, oxidation, pegylation, ISGylation, SUMOylation, ubiquitination, Neddylation, Pupylation, citrullination, deamination, deamidation, eliminylation, disulfide cleavage, or proteolytic cleavage.

In further embodiments, the PTM node 108 may comprise one database or multiple databases acquired through proteomics as will be apparent to one skill in the art. Proteomics may include western blot analysis, enzyme-linked assays, suspension bead assays, immunohistochemical staining, immunofluorescence staining, enzyme linked immunosorbent assay, mass spectrometry, matrix-assisted laser desorption/ionization (MALDI) spectrometry, time of flight (TOF) spectrometry, MALDI-TOF spectrometry, electrospray ionization (ESI) spectrometry, protein chips, reverse-phase protein microarrays, ion mobility spectrometry or any other method of measuring protein amount as apparent to one skilled in the art.

Figure 1B:
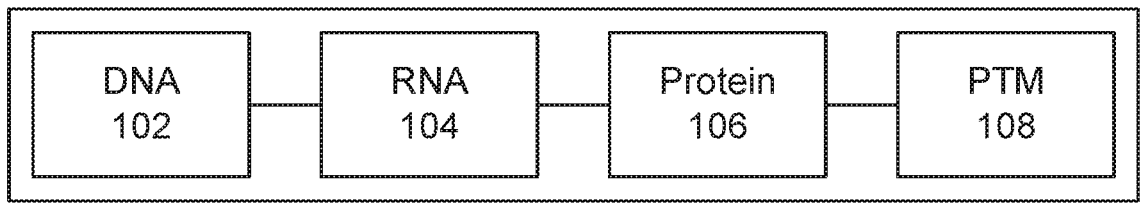
FIG. 1B depicts an interaction between a network 100 and network 120, in accordance with an example of the present disclosure.
Figure 1B:
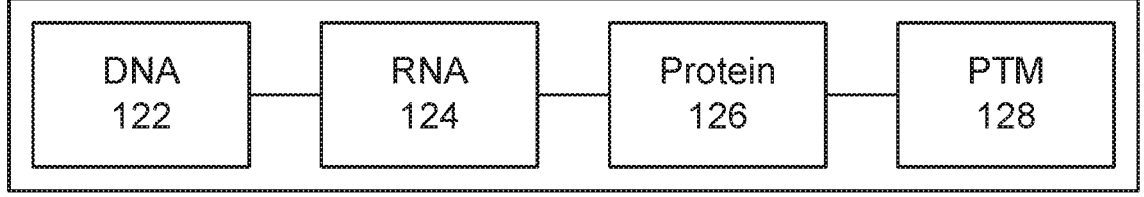

In some embodiments, network 100 may provide a recommendation to patients or doctors for disease treatment. In additional embodiments, network 100 may interact with at least one additional network to provide the recommendation to patients or doctors for disease treatment. FIG. 1B depicts a multi-network interaction according to an embodiment of the invention. Referring to FIG. 1B, network 100 may include at least one of the DNA node 102, the RNA node 104, the protein node 106, or the PTM node 108, as described above, wherein the network 100 interacts 110 with a network 120. The interaction 110 may occur between one or ore of the nodes of network 100 and network 120. In a further embodiment, network 120 may include at least one of a DNA node 122, an RNA node 124, a protein node 126, or a PTM node 128. The DNA node 122, the RNA node 124, the protein node 126, and the PTM node 128 are fully described as above. This multi-network interaction depicted in FIG. 1B is not limited to two networks as shown and described, but can include a plurality of networks, each of which may or may not interact.

Figure 1C:
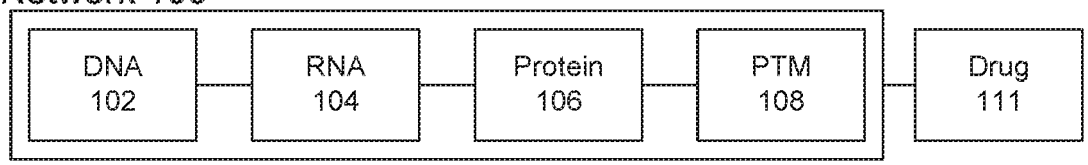
FIG. 1C depicts the drug 111 interacting with the network 100, in accordance with an example of the present disclosure.

In some embodiments, a drug having therapeutic benefit may alter the expression, amount, or activity at one or more nodes of a network. As depicted in FIG. 1C, the drug 111 interacts with the network 100. In some embodiments, drug 111 may interact with network 100 at the DNA node 102, the RNA node 104, the protein node 106, or the PTM node 108 either alone or in any combination thereof.

In some embodiments, the drug having therapeutic benefit may include an FDA approved therapeutic. In additional embodiments, the drug having therapeutic benefit may include a non-FDA approved therapeutic. In some embodiments, the drug having therapeutic benefit may include a therapeutic used to treat a patient having a disease. In additional embodiments, the drug having therapeutic benefit has a known mechanism of action. In further embodiments, the drug having therapeutic benefit alters the expression, amount, or activity of a DNA node, an RNA node, a protein node, a PTM node, or a combination thereof.

Figure 1D:
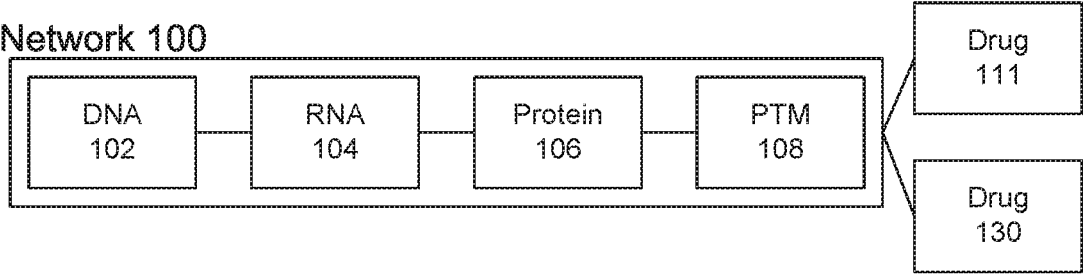
FIG. 1D depicts the drug 111 and the drug 130 interacting with the network 100, in accordance with an example of the present disclosure.

In some embodiments, a plurality of drugs having therapeutic benefit may alter the expression, amount, or activity at one or more nodes of a network. As depicted in FIG. 1D, the drug 111 and a drug 130 interact with the network 100. In some embodiments, drug 111 or drug 130 may interact with network 100 at the DNA node 102, the RNA node 104, the protein node 106, or the PTM node 108 either alone or in any combination thereof.

Figure 1E:
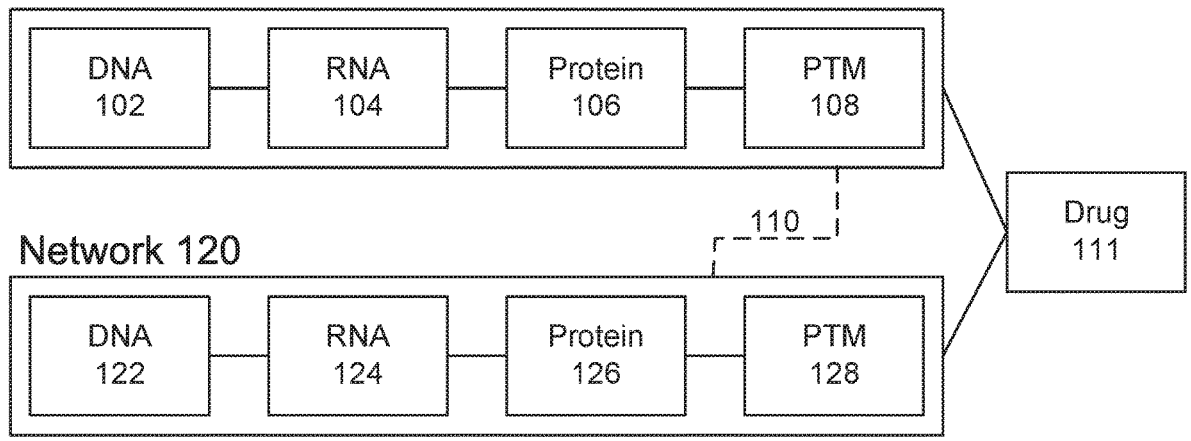
FIG. 1E depicts the drug 111 interacting with a plurality of networks, in accordance with an example of the present disclosure.

In some embodiments, a drug having therapeutic benefit may alter the expression, amount, or activity at one or more nodes of one or more networks, wherein the one or more networks interact. As depicted in FIG. 1E, the drug 111 interacts with the network 100 and the network 120 either simultaneously or in sequential order, wherein network 100 and network 120 interact 110. The interaction 110 may occur between one or more of the nodes of network 100 and network 120. In some embodiments, drug 111 may interact with network 100 at the DNA node 102, the RNA node 104, the protein node 106, or the PTM node 108 either alone or in any combination thereof. In some embodiments, drug 111 may interact with network 120 at the DNA node 122, the RNA node 124, the protein node 126, or the PTM node 128 either alone or in any combination thereof.

Figure 1F:
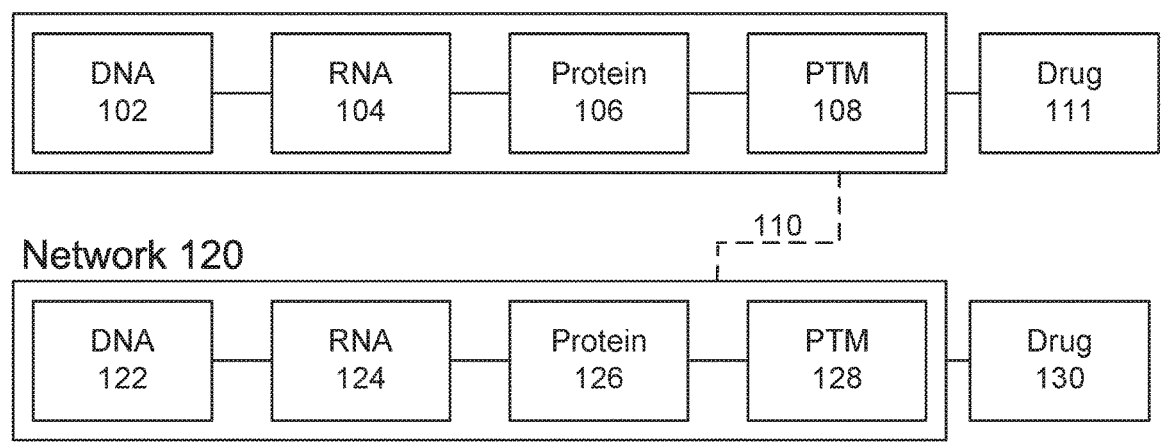
FIG. 1F depicts a plurality of drugs interacting with a plurality of networks, in accordance with an example of the present disclosure.

In some embodiments, a plurality of drugs having therapeutic benefit may alter the expression, amount, or activity at one or more nodes of one or more networks, wherein the one or more networks interact. As depicted in FIG. 1F, the drug 111 interacts with the network 100, and drug 130 interacts with the network 120 either simultaneously or in sequential order. In some embodiments, drug 111 may interact with network 100 at the DNA node 102, the RNA node 104, the protein node 106, or the PTM node 108 either alone or in any combination thereof. In some embodiments, drug 130 may interact with network 120 at the DNA node 122, the RNA node 124, the protein node 126, or the PTM node 128 either alone or in any combination thereof. In some embodiments, network 100 and network 120 interact 110. The interaction 110 may occur between one or more of the nodes of network 100 and network 120.

Example 1: HER2 Network Interacts with PIK3 Network

Figure 2:
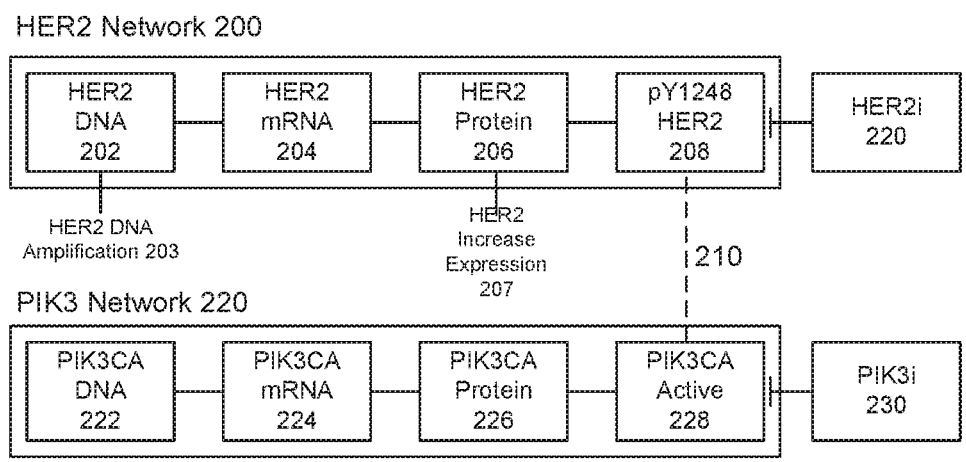
FIG. 2 depicts an interaction 210 between a HER2 Network 200 and a PIK3 Network 220, in accordance with an example of the present disclosure.

FIG. 2 depicts a receptor tyrosine-protein kinase (HER2) network 200 that interacts with a phosphoinositide 3-kinase (PIK3) network 220 according to an embodiment for recommending disease treatment for patients or doctors. As appreciated by one skilled in the art, HER2 is also known as receptor tyrosine-protein kinase ERBB2. As is also appreciated by one skilled in the art, a HER2 DNA 202 may transcribe a HER2 mRNA 204. The HER2 mRNA may be translated to a HER2 protein 206. The HER2 protein 206 may be post-translationally modified by a phosphorylation at a tyrosine 1248 of HER2 (pY1248 HER2) 208.

As will further be appreciated by one skilled in the art, a phosphatidylinositol-4,5-bisphosphate 3-kinase catalytic subunit alpha (PIK3CA) DNA 222 nay transcribe a PIK3CA mRNA 224. The PIK3CA mRNA may be translated to a PIK3CA protein 226. The PIK3CA protein 226 may be post-translationally modified which may confer an active PIK3CA 228.

In some embodiments, the HER2 DNA 202 can be amplified 203 which may occur in a patient having a disease. In some embodiments, the disease is a cancer. In further embodiments, the HER2 DNA amplification 203 may alter or increase the amount, expression, activity, or a combination thereof, of the HER2 mRNA 204 or HER2 protein 206. As depicted in FIG. 2, the HER2 DNA amplification 203 may cause a HER2 increase expression 207.

In some embodiments, a disease may alter or increase the amount, expression, activity, or a combination thereof, of the HER2 DNA 202, the HER2 mRNA 204, the HER2 protein 206, the pY1248 HER2 208, or a combination thereof.

In some embodiments, the HER2 increase expression protein 207 may occur in a patient having a disease. In some embodiments, the disease is a cancer. In further embodiments, the HER2 increase expression 207 may alter or increase the amount, expression, activity, or a combination thereof, of the pY1248 HER2 208, In some embodiments, the pY1248 HER2 208 may occur in a patient having a disease. In some embodiments, the disease is a cancer. In further embodiments, the disease may alter or increase the amount, expression, activity, or a combination thereof of the pY1248 HER2 208.

In some embodiments, the disease may alter or increase the amount, expression, activity, or a combination thereof of the PIK3CA DNA 222, the PIK3CA mRNA 224, the PIK3CA protein 226, the active PIK3CA 228, or a combination thereof.

In some embodiments, the pY1248 HER2 208 may alter or increase the amount, expression, activity, or a combination thereof of the active PIK3CA 228 through interaction 210.

In some embodiments, a HER2 inhibitor (HERi) 220 having therapeutic benefit is administered to a patient and may alter the expression, amount, or activity of one or more of the HER2 DNA 202, the HER2 mRNA 204, the HER2 protein 206, the pY1248 HER2 208, or a combination thereof.

In some embodiments, a PIK3 inhibitor (PIK3i) 230 having therapeutic benefit is administered to a patient and may alter the expression, amount, or activity of one or more of the PIK3CA DNA 222, the PIK3CA mRNA 224, the PIK3CA protein 226, the PIK3CA 228, or a combination thereof.

As noted above, based upon the network graph representations of the cellular signaling pathways as shown, for example, in FIG. 2, a proximity based distance between each mapped node and a drug target node can be computed and a score for each mapped node, as it corresponds to the drug target nodes, can be extracted. For example, for networks 200 and 220 as shown in FIG. 2, the distance metrics can be computed as:

$$dist(ERBB2\ amp, HER2i)=4$$

$$dist(HER2\ high\ exp, HER2i)=2$$

$$dist(HER2pY1248, HER2i)=1$$

Based upon these distance metrics, scores can be determined. For example, the scores can be the inverse of the distance measurement, To continue the above example:

$$score(ERBB2\ amp, HER2i)=\frac{1}{4}$$

$$score(HER2\ high\ exp, HER2i)=\frac{1}{2}$$

$$score(HER2\ pY1248, HER2i)=1$$

Thus, as shown in this example, the interaction between the pY128 HER2 phosphoprotein and HER2i has the highest score and, as such, provides for a higher weighting of the phosphoprotein data than other molecular data when generating a single molecular score.

As noted above, once the weights for various molecular data have been determined, an algorithm can be used to refine the weights based upon, for example, outcomes data. In certain implementations, the outcome data can include values for overall survival, progression-free survival on a specific drug, and/or response rate to a specific drug.

The algorithm as described herein can include machine learning or other similar statistical-based modeling techniques. For example, the algorithm used may depend on an expected outcome of the algorithm. For example, a processing device can be configured to use a first process or algorithm to calculate refinements to a derived weight as described above based upon a first set of outcomes data while using a second or different process/algorithm to calculate refinements to a derived weight as described above based upon a second set of outcomes data. Different methods and algorithms may be used to calculate the refined weights in concert or substantially simultaneously. The output of each of the different methods and algorithms can then be compared/further analyzed to determine which output is highest rated, or the output of each method and algorithm can be combined into a combinational metric.

In some implementations, a machine learning model as described in further detail below can be trained on a large population, for example, a population that can range from several thousand to tens of thousands of patient records comprising electrophysiology, demographic and medical history information. The machine learning tool can include but is not limited to penalized regression/classification techniques such as random forest and gradient boosting, (e.g., implemented using R or any other statistical/mathematical programming language), Bayesian belief networks, and collaborative filters. Any other classification based machine learning tool can be used, including neural networks (as described in more detail below) and support vector machines. Because the machine learning tool may be computationally intensive, some or all of the processing for the machine learning tool may be performed on a server that is separate from the medical device.

An overview of how a random forest tool may be applied to a given dataset can illustrate how a classification tool may work in interpreting given input data. A random forest is a collection of decision trees. A decision tree is a flow chart-like structure in which each node represents a test on a metric and each branch represents the outcome of the test. The tree culminates in a classification label, e.g., a decision taken at the end after computing each of the metrics. Each tree in a random forest tool gets a "vote" in classifying a given set of metrics. There are two components of randomness involved in the building of a random forest. First, at the creation of each tree, a random subsample of the total data set is selected to grow the tree. Second, at each node of the tree, a "splitter variable" is selected and the underlying patients are separated into two classes. For example, patients in one class (e.g., positive response to a specific drug) can be separated from those in another class (e.g., negative response to a specific drug). The tree is grown with additional splitter variables until all terminal nodes (leaves) of the tree are purely one class or the other. The tree is "tested" against patient records that have been previously set aside.

Each patient testing record traverses the tree, going down one branch or another depending on the metrics included in the record for each splitter variable. The patient testing record is assigned a predicted outcome based on where the record lands in the tree (a vote). The entire process may be repeated with new random divisions of the underlying dataset to produce additional trees and ultimately a "forest". In each case, a different subset of patients can be used to build the tree and test its performance In developing the results described in the below example implementation, a predetermined number of model variations are trained. For example, each model variation is labeled sequentially, (e.g., for 100 runs, labeled from 1-100). In each run of the model, the software randomly samples a predetermined portion (e.g. an 80% portion) of the population as the training set and sets aside the remainder (e.g., 20%) as the validation set.

As noted above, the machine learning tool can train the model on a first portion of the underlying dataset, and validate the model on a second portion of the dataset or on another separate dataset. When evaluating the performance of each model, the performance of the underlying decisions within the decision trees in the random forest can be evaluated based on specificity and sensitivity parameters. For example, the sensitivity parameter can be based on a measure of the model's ability to correctly predict whether a patient is at risk of reacting negatively to a drug treatment For example, the sensitivity parameter may be based on a proportion of patients who are treated that the model correctly predicts will react negatively to the treatment. The specificity parameter can be based on the proportion of patients who to be treated with a specific drug, and who are predicted by the relevant model as reacting positive to the drug treatment. It may be advantageous to optimally balance individual performance variables such as sensitivity and specificity at a high level. For example, by setting the specificity at a relatively high value, e.g., 95%, the underlying thresholds within the classifier model may be adjusted to minimize false positives. After the specificity is defined, the measure of sensitivity can be treated as a type of performance measure, e.g., generally in the range of 15-35% for a given model, however, smaller or larger values of sensitivity are also possible.

A validation protocol, for example, as described below, can be employed to validate the predictive performance of trained models. In an implementation, the validation phase can be used to ascertain appropriate threshold scores for classifying future patients (where an outcome is currently unknown and a prediction of the outcome is desired) and to determine the predictive performance of each classifier model generated by the machine learning tool. For validating the various models and associated threshold scores, a second group of individuals, e.g., a validation population (or cohort), can be used. For example, the validation population used can be a new validation population. The outcome for the patients in the validation cohort is eventually learned as these patients progress through treatment. In an embodiment, the patients in the validation population can be different from the group of training and test patients described above for training the model. For example, a validation population of patients and their associated metrics (validation metrics) can be independent from a training population of patients and associated metrics (training metrics). In some implementations, there may be an overlap between the validation metrics and the training metrics.

In some implementations, the validation population can be updated by at least one of 1) adjusting one or more of the metrics in the validation metrics, and 2) expanding the validation metrics based on appending additional one or more subjects to population of subjects that make up the validation population. The thresholds for classifying future patients can be refined based on the updated validation metrics. For example, metrics of a patient that is currently being treated or monitored or has otherwise not progressed through the treatment can be used to adjust the one or more metrics in the validation metrics or the patient's metrics can be added to the validation population as metrics from a new subject. The validation metrics can be adjusted as new metrics for the patient are determined during the monitoring or treatment of the patient. In some examples, as a monitored patient progresses through treatment, the patient's metrics can be added to the validation population and/or used to adjust the metrics in the validation metrics after the patient has progressed through the treatment.

In some implementations, the training population can be updated by at least one of 1) adjusting one or more of the metrics in the training metrics, and 2) expanding the training metrics based on appending additional one or more subjects to the first plurality of subjects. The machine learning classifier models can be retrained based on the updated training metrics. For example, as additional patient metrics are determined from current patients and/or metrics from new patients are determined, the machine learning model can be retrained, e.g., on the increased number of metrics or on new, different metrics, to provide updated classifier models. The training population can be updated as new metrics for current patients and/or metrics for new patients are determined or after patients have progressed through treatment.

Figure 3:
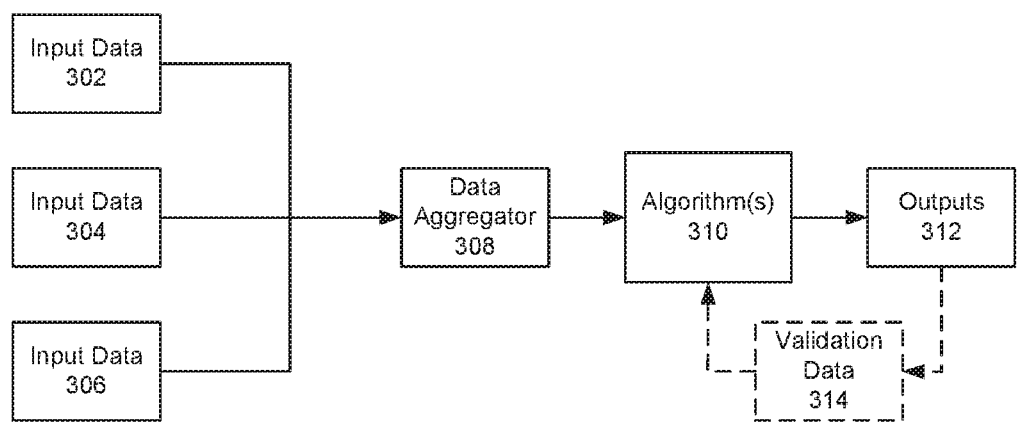
FIG. 3 depicts a sample algorithm incorporating machine learning, in accordance with an example of the present disclosure.

FIG. 3 illustrates a sample flow for training and validating one or more classifier models for a machine learning algorithm as described above. A set or population of known input data 302, 304, 306 can be provided as the data set used to train and validate the classifier models. For example, the known patient records data set may include 1000 patients that have been diagnosed with a specific ailment, their drug treatment regimens, and the associated outcomes for each patient. A percentage of the known patient data records can be used as the input data 302, 304, 306. For example, 80%, or 800, of the patient records can be used as the input 302, 304, 306.

The input data 302, 304, 306 can be fed into a data aggregator 308. The data aggregator 308 can be configured to match patient data into a single training input for the machine learning algorithm and configure the training input into a format readable by the machine learning algorithm. The data aggregator can feed the training data into algorithm 310. The algorithm 310 can include one or more untrained data structures such as a series of data trees (e.g., organized using a random forest tool as described above). Using the training input variables and known outcomes from the input data 302, 304, 306, the algorithm 310 can iteratively process each data point in the training set, thereby training the data structures to more accurately produce the expected (and known) outcomes.

Once the algorithm 310 has exhausted the input data 302, 304, 306, the algorithm can generate one or more outputs 312. The outputs 310 can be compared against the expected output (as know from the initial population) to determine the specificity and sensitivity of the now-trained algorithm 310. In certain implementations, validation data 314 can be used to further refine the trained algorithm 310 using additional patient records. For example, the validation data 314 can be input into a validation module for validation of the one or more trained algorithms 310. To continue the above example, the validation data 314 can include 200 patient records. Typically, there is no overlap between a training data set and a validation data set as there is no advantage to running the same data set twice.

As the validated classifier models as used to classify new patients (e.g., to produce new outputs for a set of patient metrics as described herein), the produced outcomes can be used to better validate the process using a closed loop feedback system. For example, as a patient is classified and treated, the result of that treatment can be included in the patient record and verified by, for example, the patient's physician. The patient's record, now updated to include a known outcome, can then be provided as feedback to the validation module. The validation module can process the feedback, comparing a generated output against the known outcome for the patient. Based upon this comparison, the validation module can further refine the validated algorithms, thereby providing a closed loop system where the models are updated and upgraded regularly.

Figure 4:
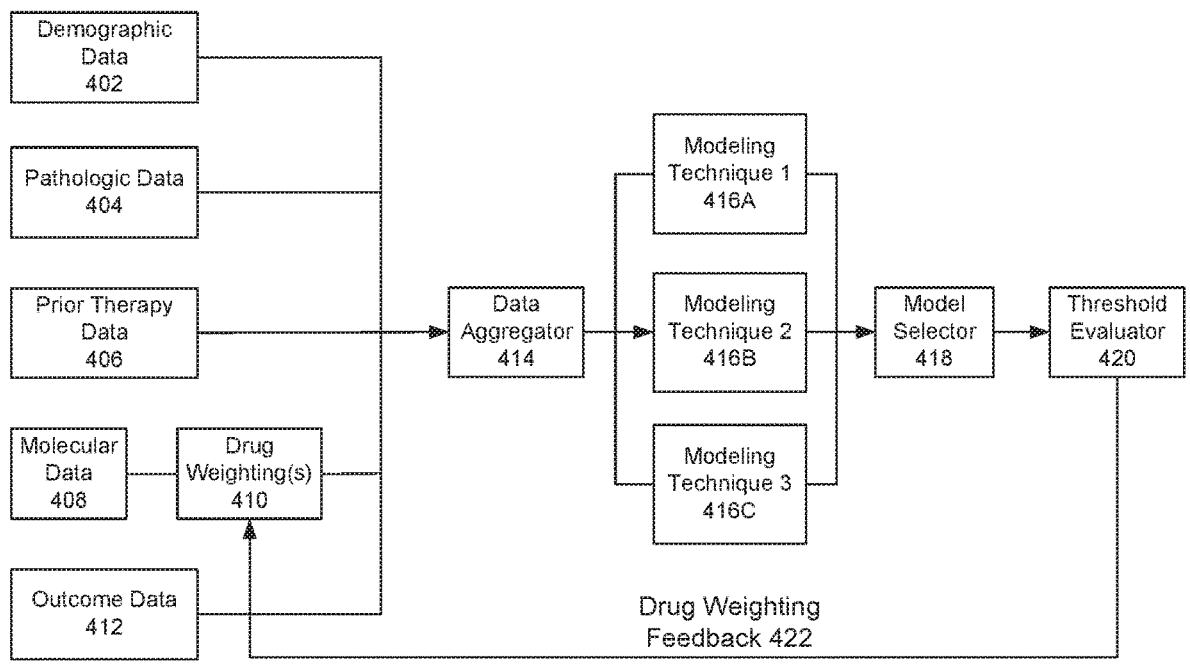
FIG. 4 depicts an algorithm for model training and adjustment of drug weighting for recommendations, in accordance with an example of the present disclosure.

FIG. 4 illustrates a flow for evaluating and potentially refining drug weightings according to the techniques and processes as described herein. Similar to the flow as shown in FIG. 3, a set of variable parameters and/or metrics can be provided as input data. For example, the input data can include demographic data 402 for a patient, pathologic data 404 for the patient, prior therapy data 406 for the patient, molecular data 408 for the patient, and outcome data 412. As further shown in FIG. 4, the drug weightings 410 as determined above can be included with the molecular data 408.

The various input data can be passed to a data aggregator 414. As above, the data aggregator can be configured to match patient data into a single input data set for the machine learning algorithm(s) and configure the input data set into a format readable by the machine learning algorithm (s). The data aggregator 414 can then pass the input data to the algorithm(s). As shown in FIG. 4, the algorithm can include a number of modeling techniques. For example, the algorithm can include modeling technique 1 416A, modeling technique 2 416B, and modeling technique 3 416C. Each of the individual modeling techniques can be modeled individually using, for example, cross-validation for parameter tuning as needed. In certain implementations, the modeling techniques can include, but are not limited to, penalized regression/classification techniques, Bayesian belief networks, and collaborative filters.

The output of the modeling techniques can be passed to a model selector 418. The model selector 418 can be configured to determine which of the model techniques is the best performing model. This determination can be based upon matching the model outputs against known outcome data to determine which model is the best performing. In certain implementations, the selector 418 can be further configured to evaluate each output of the modeling techniques and, if two or more of the outputs satisfy a particular parameter (e.g., a specific quality or performance threshold), the selector can combine the model outputs into a single output.

The output of the selector 418 can be passed to a threshold evaluator 420. The threshold evaluator 420 can be configured to determine if the output of the selector 418 is above a specific threshold. For example, the threshold evaluator 420 can compare a confidence value against a particular confidence threshold for a particular drug treatment regimen. If the confidence value does not exceed the threshold, the threshold evaluator 420 may provide drug weighting feedback 422 such that the initial drug weightings 410 are adjusted. The drug weightings can be adjusted, for example, based on a set of rules for permissible changes and/or refinement to the drug weightings. The flow as shown in FIG. 4 can then be repeated until the threshold evaluator 420 determines that the modeling output is above a particular threshold and that no additional drug weighting refinement is required.

Figure 5:
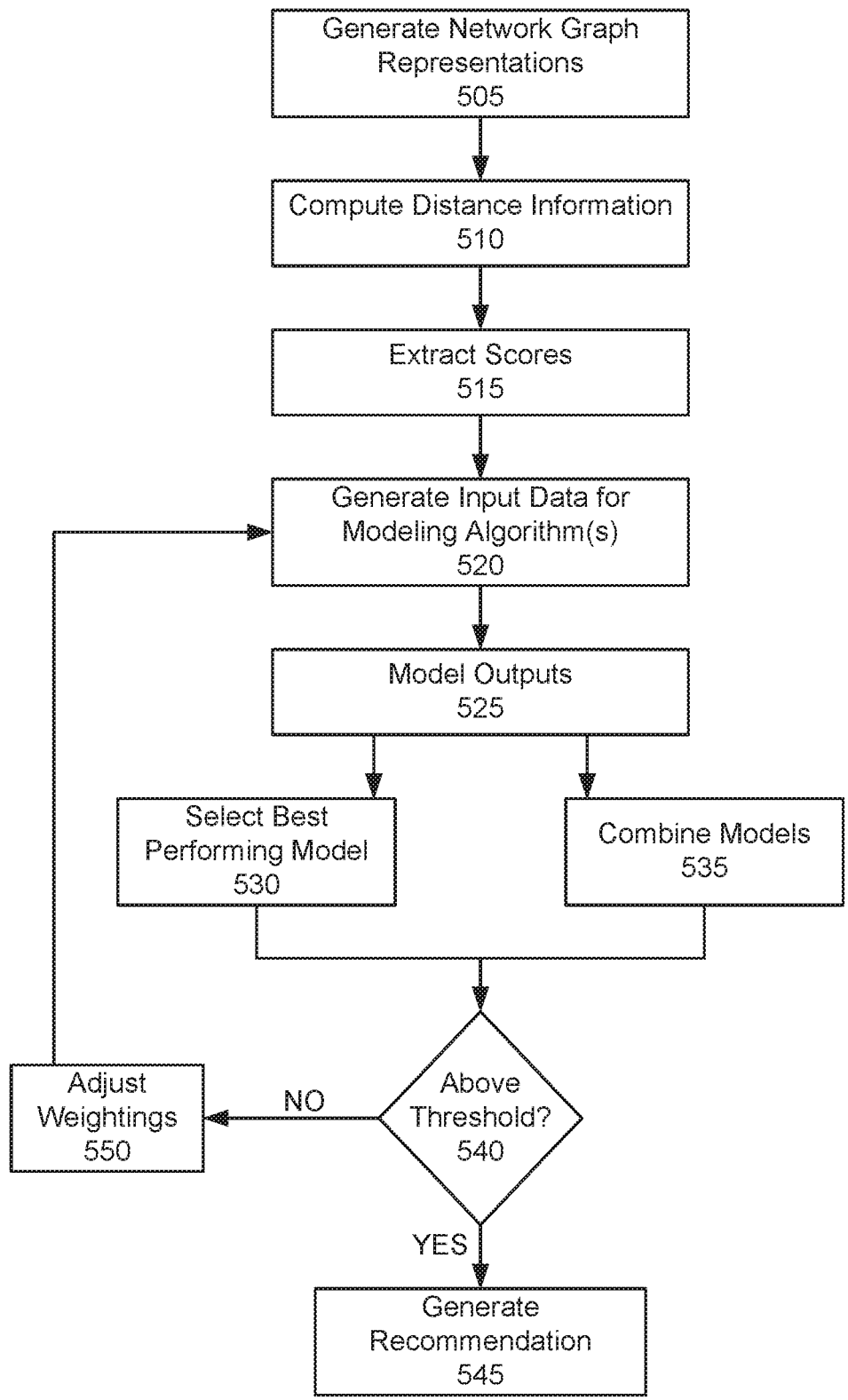
FIG. 5 depicts a sample process for determining a treatment recommendation, in accordance with an example of the present disclosure.

FIG. 5 illustrates a sample process flow for the processes and techniques as described herein. Initially, the process includes generating 505 a network graph representation of cellular signaling pathways similar to those as shown in FIG. 2. Based upon the pathways, the process includes computing 510 a network proximity-based distance for each mapped node within the network. The process further includes extracting 515 drug weighting scores for each node based upon the computed proximity-based distances.

Following the score extraction, the process as shown in FIG. 5 mirrors the flow as shown in FIG. 4. A set of input date, including the drug weighting scores, can be generated 520 for one or more modeling algorithms. The inputs can be modeled 525 using the one or more modeling algorithms As noted above, the process can include selecting 530 the best performing model or combining 535 the models into a single modeling output.

The process can include determining 540 whether the modeling output is above a particular threshold. If the modeling output is above a particular threshold, the process can generate 545 a recommendation score for a drug treatment. If the modeling output is below the threshold, the process can include adjusting 550 the drug weightings and the process can generate updated input data for the modeling algorithm(s). The modeling and modeling output evaluation can then be repeated until the modeling output exceeds the threshold.

It should be noted that the process as shown in FIG. 5 is provided by way of example only. Additional steps can be performed or shown steps can be eliminated and/or combined based upon the implementation of the techniques and processes as described herein.

Figure 6:
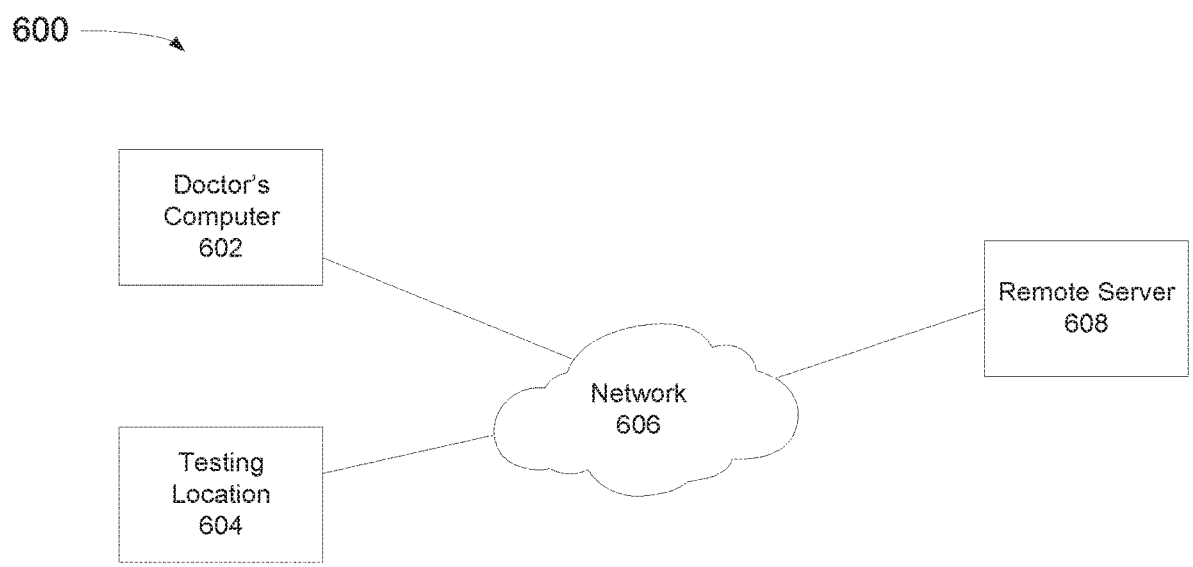
FIG. 6 depicts a sample network overview, in accordance with an example of the present disclosure.

FIG. 6 illustrates a sample computer network 600 depicting a sample topology illustrating how one or more computer systems or terminals can be operably connected to a remote server. As shown in FIG. 6, a doctor's computer 602 and a computing device located at a testing location 604 (e.g., a location preforming one or more test related to a patient) can be operably connected to a monitoring server 608 through network 606. In certain implementations, information related to the patient such as various patient metrics and parameters as described herein (e.g., demographic information, pathologic information, prior therapy information, and molecular information including drug weightings) can be transmitted from one or both of the doctor's computer 602 and the testing location computer 604 to the remote server 608. Additional information, such as the outcomes information, can be remotely stored on the remote server 608. Based upon receiving/accessing the various patient information, the remote server 608 can be configured to perform one or more algorithms as described herein to provide for a treatment recommendation for a specific patient.

Figure 7:
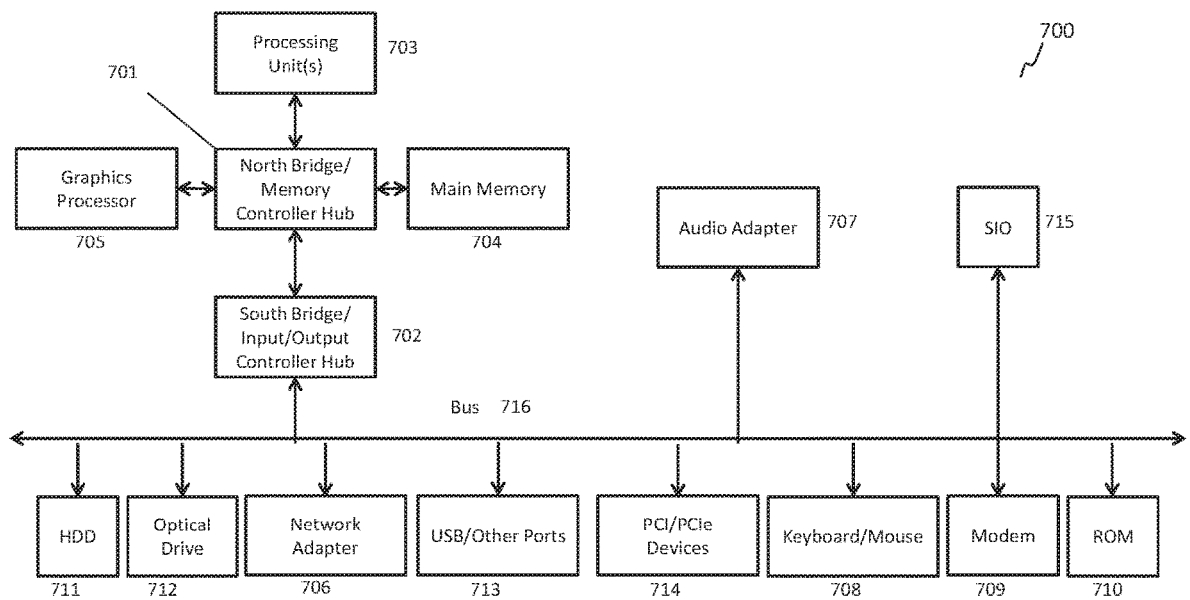
FIG. 7 depicts an illustrative computer system.

FIG. 7 is a block diagram of an illustrative data processing system 700 in which aspects of the illustrative embodiments are implemented. Data processing system 700 is an example of a computer, such as a server (e.g., remote server 608) or client, in which computer usable code or instructions implementing the process for illustrative embodiments of the present invention are located. In some embodiments, the data processing system 700 may be a server computing device.

In the depicted example, data processing system 700 can employ a hub architecture including a north bridge and memory controller hub (NB/MCH) 701 and south bridge and input/output (I/O) controller hub (SB/ICH) 702. Processing unit 703, main memory 704, and graphics processor 705 can be connected to the NB/MCH 701. Graphics processor 705 can be connected to the NB/MCH 701 through, for example, an accelerated graphics port (AGP).

In the depicted example, a network adapter 706 connects to the SB/ICH 702. An audio adapter 707, keyboard and mouse adapter 708, modem 709, read only memory (ROM) 710, hard disk drive (HDD) 711, optical drive (e.g., CD or DVD) 712, universal serial bus (USB) ports and other communication ports 713, and PCI/PCIe devices 714 may connect to the SB/ICH 702 through bus system 716. PCI/PCIe devices 714 may include Ethernet adapters, add-in cards, and PC cards for notebook computers. ROM 710 may be, for example, a flash basic input/output system (BIOS). The HDD 711 and optical drive 712 can use an integrated drive electronics (IDE) or serial advanced technology attachment (SATA) interface. A super I/O (SIO) device 715 can be connected to the SB/ICH 702.

An operating system can run on processing unit 703. The operating system can coordinate and provide control of various components within the data processing system 700. As a client, the operating system can be a commercially available operating system. An object-oriented programming system, such as the Java™ programming system, may run in conjunction with the operating system and provide calls to the operating system from the object-oriented programs or applications executing on the data processing system 700. As a server, the data processing system 700 can be an IBM® eServer™ System p® running the Advanced Interactive Executive operating system or the Linux operating system. The data processing system 700 can be a symmetric multiprocessor (SMP) system that can include a plurality of processors in the processing unit 703. Alternatively, a single processor system may be employed.

Instructions for the operating system, the object-oriented programming system, and applications or programs are located on storage devices, such as the HDD 711, and are loaded into the main memory 704 for execution by the processing unit 703. The processes for embodiments described herein can be performed by the processing unit 703 using computer usable program code, which can be located in a memory such as, for example, main memory 704, ROM 710, or in one or more peripheral devices.

A bus system 716 can be comprised of one or more busses. The bus system 716 can be implemented using any type of communication fabric or architecture that can provide for a transfer of data between different components or devices attached to the fabric or architecture. A communication unit such as the modem 709 or the network adapter 706 can include one or more devices that can be used to transmit and receive data.

Those of ordinary skill in the art will appreciate that the hardware depicted in FIG. 7 may vary depending on the implementation. Other internal hardware or peripheral devices, such as flash memory, equivalent non-volatile memory, or optical disk drives may be used in addition to or in place of the hardware depicted. Moreover, the data processing system 700 can take the form of any of a number of different data processing systems, including but not limited to, client computing devices, server computing devices, tablet computers, laptop computers, telephone or other communication devices, personal digital assistants, and the like. Essentially, data processing system 700 can be any known or later developed data processing system without architectural limitation.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by $1/10$ of the stated values, e.g., ±10%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the claims include equivalents to the recited values, e.g., variations in the numerical quantity of such values that can occur, but would be recognized to be equivalents by a person skilled in the art.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A method for generating a recommendation for optimal drug treatment, the method comprising:
    receiving a data set comprising a plurality of patient records;
    training a machine learning algorithm using a first portion of the data set, wherein the machine learning algorithm is configured to score drug-specific treatment based on molecular data of a patient;
    calculating drug-specific treatment scores based upon network-based distances for one or more target drug nodes;
    validating the machine learning algorithm using a second portion of the data set;
    modeling one or more outputs based upon input data, wherein the input data comprises at least a portion of the drug-specific treatment scores;
    selecting an algorithmic output from the one or more modeling outputs based upon at least one performance criteria;
    calculating if the selected algorithmic output of the modeling satisfies a threshold;
    if the selected algorithmic output satisfies the threshold, generating the recommendation for drug-specific treatment associated with the patient; and
    revalidating the machine learning algorithm using the input data.

2. The method of claim 1, wherein calculating the drug-specific treatment scores comprises:
    overlaying the molecular data of the patient onto at least one network graph representation of cellular signaling pathways;
    computing a network proximity-based distance from the at least one network graph representation; and
    determining the drug-specific treatment scores based upon at least the network proximity-based distance.

3. The method of claim 2, wherein overlaying the molecular data of the patient onto at least one network graph representation comprises determining a corresponding node in the graph for each molecular result in a patient profile.

4. The method of claim 3, wherein determining a corresponding node comprises:
    mapping gene copy number changes to DNA nodes;
    mapping transcript over/under-expressions to mRNA nodes;
    mapping protein expression changes to protein nodes; and mapping phosphoprotein expression changes to active protein nodes.

5. The method of claim 4, wherein determining a corresponding node further comprises mapping one or more mutations to the active protein nodes.

6. The method of claim 4, wherein computing the network proximity-based distance comprises comparing mapped nodes to known drug target locations.

7. The method of claim 6, wherein computing the network proximity-based distance further comprises determining a shortest path between a mapped node and a known drug target location according to at least one standard graph theory methodology.

8. The method of claim 7, wherein the at least one standard graph theory methodology comprises Dijkstra's algorithm.

9. The method of claim 2, wherein calculating the drug-specific treatment scores further comprises:
extracting a minimum network-based distance for each target drug node; and
determining a drug-specific treatment score based upon the extracted minimum network-based distance.

10. The method of claim 9, wherein the drug-specific treatment score is inversely proportional to the extracted minimum network-based distance.

11. The method of claim 1, wherein modeling the one or more outputs based upon generated input data comprises:
receiving the input data;
generating a modeling input comprising at least a portion of the data set; and
modeling the one or more outputs using one or more modeling algorithms.

12. The method of claim 11, further comprising receiving outcome data, wherein the one or more modeled outputs are based upon at least a portion of the outcome data.

13. The method of claim 12, wherein the outcome data comprises at least one of survival rates for a specific drug, progression-free survival rates for a specific drug, and response rates to a specific drug for a patient population.

14. The method of claim 11, wherein the one or more modeling algorithms comprises at least one machine learning algorithm.

15. The method of claim 11, wherein the one or more modeling algorithms comprise at least one of a penalized regression/classification modeling technique, a Bayesian belief modeling technique, and a collaborative filter modeling technique.

16. The method of claim 11, wherein the input data comprises demographic data for a patient, pathologic data for the patient, prior therapy data for the patient, molecular data for the patient, and outcome data.

17. The method of claim 11, wherein generating the modeling input comprising at least a portion of the input data comprises aggregating the input data into a single modeling input.

18. The method of claim 1, wherein selecting an algorithmic output from the one or more modeling outputs based upon at least one performance criteria comprises:
comparing an output from each of one or more modeling algorithms to determine a best performance output; and
determining the algorithmic output based upon the best performance output.

19. The method of claim 1, wherein selecting an algorithmic output from the one or more modeling outputs based upon at least one performance criteria comprises:
receiving an output from each of one or more modeling algorithms;
combining the output of each of the one or more modeling algorithms to produce the a combined output; and
determining the algorithmic output based upon the combined output.

20. The method of claim 1, further comprising:
if the selected algorithmic output does not satisfy the threshold, adjusting the drug-specific treatment scores to produce refined drug-specific treatment scores.

21. The method of claim 20, further comprising:
modeling one or more updated outputs based upon updated input data, wherein the updated input data comprises at least a portion of the refined drug-specific treatment scores; and
selecting an updated algorithmic output from the one or more updated modeling outputs based upon the at least one performance criteria.

22. The method of claim 2, wherein computing the network proximity-based distance comprises weighting the network proximity-based distance based on proximity of a biomarker/molecular measurement to the mechanism of action of the drug wherein biomarkers that measure output with higher proximity to a mechanism of action to the drug are given higher weighting and biomarkers that measure output with lower proximity to the mechanism of action to the drug are given lower weighting.

23. The method of claim 22, wherein phosphoprotein data is given a highest weighting, protein is data given a second highest weighting, RNA expression is data given a third highest weighted score, and DNA data is given a least weighting.

24. A system for generating a recommendation for drug-specific treatment, the system comprising:
a processing device; and
a computer readable medium operably connected to the processing device and comprising programming instructions that, when executed, cause the processing device to:
receive a data set comprising a plurality of patient records,
train a neural network using the data set, wherein the neural network is configured to score drug-specific treatments based on molecular data of a patient,
calculate drug-specific treatment scores based upon network-based distances for one or more target drug nodes,
validate the machine learning algorithm using a second portion of the data set,
model one or more outputs based upon input data, wherein the input data comprises at least a portion of the drug-specific treatment scores,
select an algorithmic output from the one or more modeling outputs based upon at least one performance criteria,
calculate if the selected algorithmic output of the modeling satisfies a threshold,
if the selected algorithmic output satisfies the threshold, generate the recommendation for drug-specific treatment associated with the patient, and
revalidate the machine learning algorithm using the input data.

25. The system of claim 24, wherein the programming instructions for determining the drug scores comprise additional instructions that, when executed, cause the processing device to:
overlay the molecular data of the patient onto at least one network graph representation of cellular signaling pathways;

compute a network proximity-based distance from the at least one network graph representation; and determine the drug-specific treatment scores based upon at least the network proximity-based distance.

26. The system of claim 25, wherein the programming instructions for overlaying the molecular data of the patient onto at least one network graph representation comprise additional instructions that, when executed, cause the processing device to determine a corresponding node in the graph for each molecular result in a patient profile.

27. The system of claim 26, wherein the programming instructions for determining a corresponding node comprise additional instructions that, when executed, cause the processing device to:
map gene copy number changes to DNA nodes;
map transcript over/under-expressions to mRNA nodes;
map protein expression changes to protein nodes; and
map phosphoprotein expression changes to active protein nodes.

28. The system of claim 27, wherein the programming instructions for determining a corresponding node comprise additional instructions that, when executed, cause the processing device to map one or more mutations to the active protein nodes.

29. The system of claim 27, wherein the programming instructions for computing the network proximity-based distance comprise additional instructions that, when executed, cause the processing device to compare mapped nodes to known drug target locations.

30. The system of claim 29, wherein the programming instructions for computing the network proximity-based distance comprise additional instructions that, when executed, cause the processing device to determine a shortest path between a mapped node and a known drug target location according to at least one standard graph theory methodology.

31. The system of claim 30, wherein the at least one standard graph theory methodology comprises Dijkstra's algorithm.

32. The system of claim 25, wherein the programming instructions for determining the drug scores comprise additional instructions that, when executed, cause the processing device to:
extract a minimum network-based distance for each target drug node; and
determine a drug-specific treatment score based upon the extracted minimum network-based distance.

33. The system of claim 32, wherein the drug-specific treatment score is inversely proportional to the extracted minimum network-based distance.

34. The system of claim 24, wherein the programming instructions for modeling the one or more outputs based upon generated input data comprise additional instructions that, when executed, cause the processing device to:
receive the input data;
generate a modeling input comprising at least a portion of the input data; and
model the one or more outputs using one or more modeling algorithms.

35. The system of claim 34, wherein the computer readable medium further comprises additional instructions that, when executed, cause the processing device to receive outcome data, wherein the one or more modeled outputs are based upon at least a portion of the outcome data.

36. The system of claim 35, wherein the outcome data comprises at least one of survival rates for a specific drug, progression-free survival rates for a specific drug, and response rates to a specific drug for a patient population.

37. The system of claim 34, wherein the one or more modeling algorithms comprises at least one machine learning algorithm.

38. The system of claim 37, wherein the one or more modeling algorithms comprise at least one of a penalized regression/classification modeling technique, a Bayesian belief modeling technique, and a collaborative filter modeling technique.

39. The system of claim 34, wherein the input data comprises demographic data for a patient, pathologic data for the patient, prior therapy data for the patient, molecular data for the patient, and outcome data.

40. The system of claim 39, wherein the programming instructions for generating the modeling input comprising at least a portion of the input data comprise additional instructions that, when executed, cause the processing device to aggregate the input data into a single modeling input.

41. The system of claim 24, wherein the programming instructions for selecting an algorithmic output from the one or more modeling outputs based upon at least one performance criteria comprise additional instructions that, when executed, cause the processing device to:
compare an output from each of one or more modeling algorithms to determine a best performance output; and
determine the algorithmic output based upon the best performance output.

42. The system of claim 24, wherein the programming instructions for selecting an algorithmic output from the one or more modeling outputs based upon at least one performance criteria comprise additional instructions that, when executed, cause the processing device to:
receive an output from each of one or more modeling algorithms;
combine the output of each of the one or more modeling algorithms to produce the a combined output; and
determine the algorithmic output based upon the combined output.

43. The system of claim 24, wherein the computer readable medium further comprises additional instructions that, when executed, cause the processing device to:
adjust the drug-specific treatment scores to produce refined drug-specific treatment scores if the selected algorithmic output does not satisfy the threshold.

44. The system of claim 43, wherein the computer readable medium further comprises additional instructions that, when executed, cause the processing device to:
model one or more updated outputs based upon updated input data, wherein the updated input data comprises at least a portion of the refined drug-specific treatment scores; and
select an updated algorithmic output from the one or more updated modeling outputs based upon the at least one performance criteria.

45. The system of claim 25, wherein the programming instructions for computing the network proximity-based distance comprise weighting the network proximity-based distance based on proximity of a biomarker/molecular measurement to the mechanism of action of the drug wherein biomarkers that measure output with higher proximity to a mechanism of action to the drug are given higher weighting and biomarkers that measure output with lower proximity to the mechanism of action to the drug are given lower weighting.

46. The system of claim 45, wherein phosphoprotein data is given a highest weighting, protein is data given a second highest weighting, RNA expression is data given a third highest weighted score, and DNA data is given a least weighting.

* * * * *